United States Patent [19]
Villas

[11] Patent Number: 5,230,356
[45] Date of Patent: Jul. 27, 1993

[54] PERSONAL TOOTHPICK

[76] Inventor: Hugo J. Villas, 37 Nelson St., Harrington Park, N.J. 07640

[21] Appl. No.: 932,804

[22] Filed: Aug. 20, 1992

[51] Int. Cl.$^5$ .............................................. A61C 15/00
[52] U.S. Cl. .................... 132/329; 132/321; 128/62 A
[58] Field of Search ............ 132/321, 329; 128/62 A; 223/99

[56] References Cited

U.S. PATENT DOCUMENTS

| | | | |
|---|---|---|---|
| D. 199,832 | 12/1962 | Edelman et al. | 132/329 |
| 1,527,845 | 2/1925 | Daniel | 132/321 |
| 1,654,230 | 12/1927 | Zimmerman | 132/329 |
| 2,411,118 | 11/1946 | Schuster | 223/99 |
| 2,567,408 | 9/1951 | Soderberg | 223/99 |
| 3,404,707 | 10/1968 | Feld | 223/99 |
| 3,892,040 | 7/1975 | Marquis | 132/321 |
| 4,064,883 | 12/1977 | Oldham | 132/321 |
| 4,090,649 | 5/1978 | Cichinski | 223/99 |
| 4,667,860 | 5/1987 | Feuerman | 223/99 |
| 4,720,026 | 1/1988 | Feverman | 223/99 |

FOREIGN PATENT DOCUMENTS

| | | | |
|---|---|---|---|
| 828829 | 5/1938 | France | 223/99 |
| 694557 | 12/1950 | France | 132/329 |
| 505345 | 12/1954 | Italy | 223/99 |

Primary Examiner—Gene Mancene
Assistant Examiner—Frank A. LaViola
Attorney, Agent, or Firm—Richard A. Joel

[57] ABSTRACT

A personal toothpick comprises a curved handle with a thin wire hollow form at each end, designed to enter the smallest space between teeth to extract impacted food particles in between teeth and gums. The handle is of a modified s-shaped configuration with thin wire forms extending outwardly therefrom at each extremity in a set shape and being mounted to the handle at their ends.

2 Claims, 3 Drawing Sheets

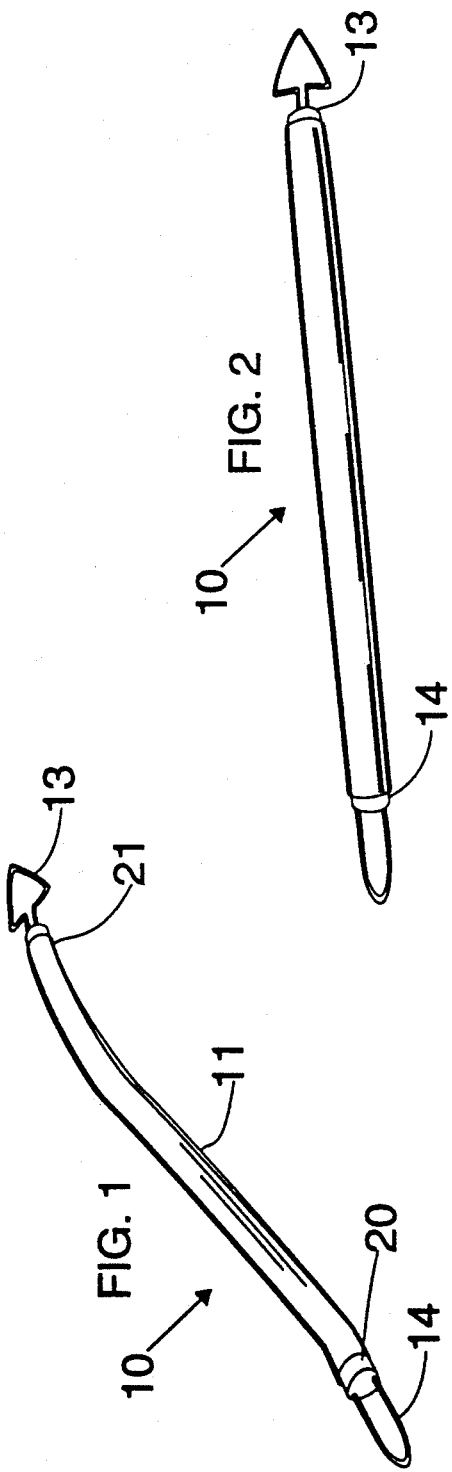
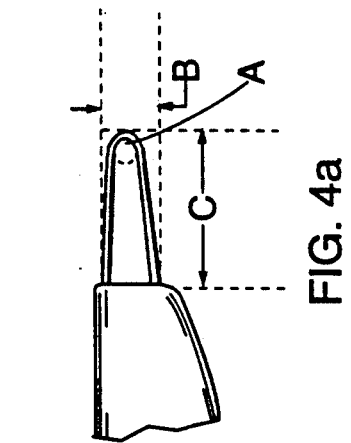
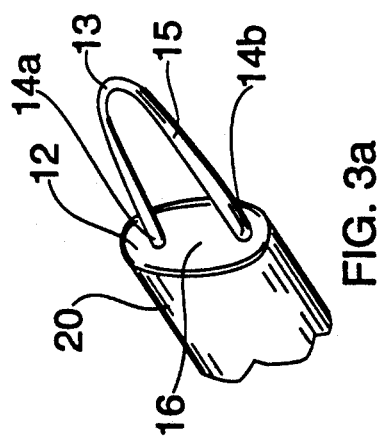

FIG. 6  TABLE OF DIMENSIONS

| HOLLOW POINT CONFIGURATION | A PIVOT DIA. | WIRE DIA. | B WIDTH | C LENGTH | D RECESS LENGTH |
|---|---|---|---|---|---|
| FIRM END | .0625 | .012 | .09375 | .34375 | -- |
| ACTIVE END | .0625 | .015 | .125 | .375 | .4375 |
| SEMI-ACTIVE END | .09375 | .015 | .10937 | .375 | .4375 |

PERSONAL TOOTHPICK

BACKGROUND OF THE INVENTION

From the earliest times, carnivore man has resorted to the use of small, sharp slivers of wood, thorns, bone, and ivory (some fire-hardened) to push, pull and extract meat and vegetable matter entrapped in between the teeth to relieve the annoyance or pain of such entrapped food. The design of these implements have not changed throughout the milleniums of their use. The design is basically a handle extending to a sharp, round or flattened point. There are museum samples of soft metal straight and curved picks made from alloys of copper, tin, lead and zinc that go back in history several thousand years. The solid points are designed in the round, flat wedge, triangle, and knife edge configurations. There are now plastic versions of these previous designs, and they have made their appearance in the past 30 to 40 years. The claimed innovative features of these later-day designs is that the working end of the pick is curved or the handle is curved to faciliate working the pick at the work site or to present the solid point at 90° to the teeth line.

There are other designs for clearing debris in between the teeth, such as cotton string in flat strands (may be waxed) called Dental Floss. This method requires a certain degree of oral and finger dexterity that is not available to everyone but is highly recommended. There are many devices that hold strands of Dental Floss taut so as to facilitate the "flossing" of the back teeth. These harp-shaped handles may also incorporate solid-point picks of various shapes and configuration at the opposite end of the flossing device. There are also machines that shoot a water jet or stream at the offending area, and the purpose of the jet is to irrigate and flush the area clean. This method is also highly recommended. Another system is the use of small conical-shaped brushes (and other configurations) that are either fixed onto or screwed onto a suitable handle. The dimensions of these brushes are such that they preclude their use in small, tight spaces comtemplated by the disclosure in the present application.

There are, of course, other known types of teeth cleaners and picks; many of these devices are complex structures and expensive to manufacture. Many of these prior art picks or devices do not provide the strength, adaptability and flexibility to work effectively and safely in small, tight spaces in between teeth as the present invention provides. The present invention, called an X-Tricator Pik TM was invented to solve the problems caused by tight, very small spaces between the teeth where the solid point picks cannot enter without causing pain or push and rupture the soft tissues to the point of bleeding. Another unsatisfactory property of solid point picks (wood, plastic or steel) are their propensity to lodge and even fracture in place due to their inherent weakness in design and material physical properties (lack of elongation, stength and/or flexibility).

An example of poor application of a good design is those steel picks that follow the designs used by professional dentists and are now in the hands of unskilled users. The instruments are usually very sharp pointed and some, sharp edged that can easily pierce gums and cut soft tissues. These instruments are intended to be guided by direct sight placement, i.e., another person (a dentist) is guiding the direction and movement of the pick. Of necessity, most picks are tapered to strengthen them along the longitudinal axis and, therfore, their cross-sectional area increases rapidly. The increase in pick thickness prevents them from penetrating effectively across the width of the tooth face. The invention described herein shows that the working ends are the same constant dimension for their entire working length across the width of the tooth.

The personal handpick is essentially guided by feel and mental imagery and, therefore, must have of necessity a blunt point without sharp edges that would otherwise cut or pierce tissue surrounding the teeth. The ideal pick enters a tight area and grasps the offending food particle or scrapes along the walls of the teeth, pushing like a bulldozer or entrapping the food particle and dragging it out as the pick is extracted from the mouth.

SUMMARY OF THE INVENTION

The present invention comprises a personal toothpick known as the X-Tricator Pik TM. The subject toothpick comprises a curved handle having a thin wire extending therefrom at each end of the handle. The handle is in a modified S-like configuration and the thin wires are shaped in a hollow form with both ends fixed to the handle. The wire forms may have several shapes as shown in the several preferred embodiments of the drawings.

Accordingly, an object of this invention is to provide a new and improved personal toothpick. Another object of this invention is to provide a new and improved toothpick having wire form ends mounted to the handle at each end.

A more specific object of this invention is to provide a new an improved personal toothpick having an S-shaped handle with predetermined thin wire loop ends in a predetermined configuration to catch and remove particles from between one's teeth.

BRIEF DESCRIPTION OF DRAWINGS

Other objects and advantages of the present invention may be more clearly seen when viewed in conjunction with the accompanying drawings wherein:

FIG. 1 is a perspective view of the invention;

FIG. 2 is a top view of the invention;

FIG. 3a is an enlarged perspective view of a firm end wire embodiment of the invention;

FIG. 4a–c are top views of the invention embodiment shown in FIGS. 3a–c with the dimensions noted by letters which relate to dimensions shown in FIG. 6;

FIG. 6 is a table of dimensions for the various embodiments of the invention.

DETAILED DESCRIPTION OF INVENTION

Figure 3B:
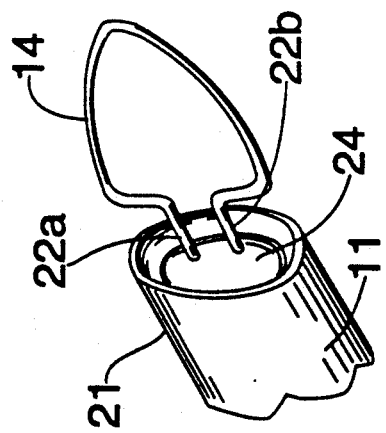
FIG. 3b is an enlarged view of an active end wire configuration embodiment of the invention.

Reference is made to the drawings to follow the detailed description of the invention. The personal toothpick 10 or X-Tricator Pik TM has a handle 11 shaped in a soft "S" configuration in the longitudinal direction, with an oval cross-sectional area 12 for easy grasping by the fingers. At one end 20 shown in FIG. 2, a narrow "V" shaped thin wire loop 13, with both ends 14a, 14b of the wire 15 fixed into the end of the handle 11. As shown in FIG. 3b, the opposite end 21 of handle 11 includes another "V" shaped thin wire loop 14, but broader in profile, with each end 22a, 22b of the wire loop 14 fixed into the handle 11 in a recess 24 back in the handle 11 to allow flexing the sides of the loop 14. This end 21 is identified as the "active" end and the previous end 20 as the "firm" end.

Figure 3C:
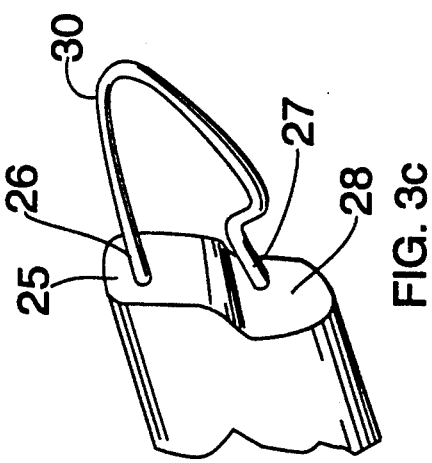
FIG. 3c is an enlarged view of a semi-active wire end embodiment of the invention.
Figure 5:
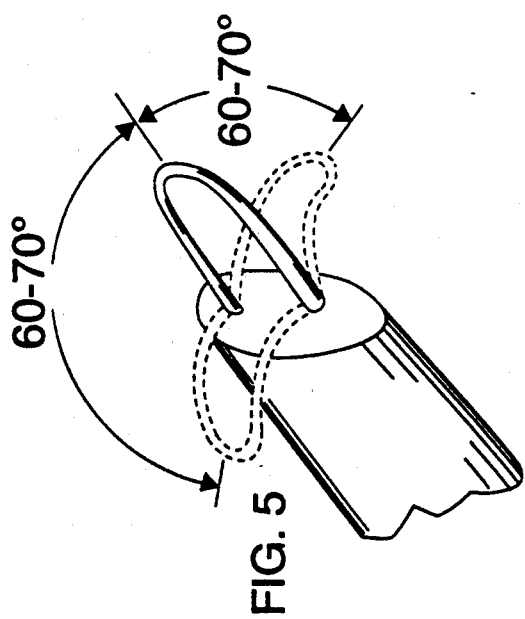
FIG. 5 is an enlarged perspective view of the invention showing the flexibility of the wire loop end.

FIG. 3c shows another variation in the hollow-point design, wherein one leg 26 of the hollow point loop 30 is fixed at the handle end 25 and the other leg 27 is fixed or imbedded at the end of a recess or cavity 28 that extends into the handle 11. This arrangement is known as a "semi-active" end.

The two wire loops 13, 14 form hollow points, the innovative design feature of this invention. These slim, thin, flexible hollow points are the distinguishing feature of the invention and are the means providing the effective and efficient way the pick performs its assigned function. The pick handle 11 is grasped by the thumb, fore and middle fingers and directed to the area in the mouth, where it is expected that the pick 10 will extract food particles and entrapped matter in between teeth and gums. The configuration of the handle 11 and the hollow points are designed to enter the teeth at approximately 90° to the face or side of the teeth. The wire hollow-point loop 13, 14 or 30 is gently inserted in the space between the two teeth and is moved in and out, up and down. The hollow-points will pass into areas that are too small for most or all the conventional toothpicks presently available. As the wire hollow point moves further into the space, it pushes particles out in front and, at the same time, it captures the entrapped food particle inside the wire loop 13, 14 or 30 so that when the pick 10 is pulled out it will drag out the food particles like no other toothpick can or does.

The wire hollow point is flexible in relation to the handle 11, and there is no fear of the pick breaking and leaving the loop 13, 14 or 30 behind lodged in between the teeth. The flexible feature of the hollow points will allow for small, overt or exaggerated movement of the manipulating hand working on the problem without harming the gums or teeth. The wire hollow points will not puncture or cut the gums. All surfaces of the working end are round and smooth and will not scratch, scrape or damage the enamel surface of the tooth or any crown or filling materials, whether resin, metallic or ceramic in nature. If the pick pressure is excessive, the user will experience pain well before any damage is done to tissue or gum. Where the space in between the teeth is very small, the "semiactive" (FIG. 3c) and/or "active" (FIG. 3b) hollow point loop 30 and 14 respectively will collapse the point to the smallest configuration possible and permit it to enter the entire width of the teeth to push or pull out entrapped particles.

Figure 4B:
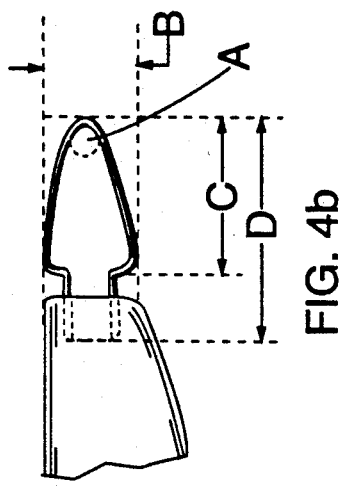
Figure 4C:
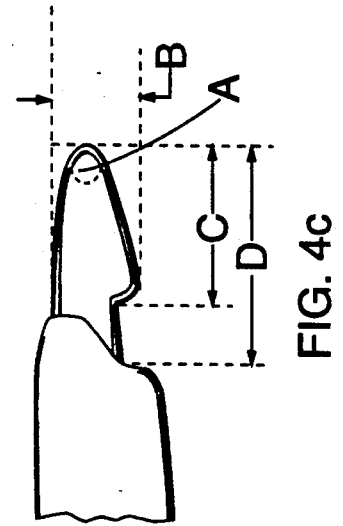

The dimensions referred to in the Table FIG. 6 are clearly depicted and labeled in FIGS. 4 a–c, where wire DIA represents the diameter of the wire; A the circle diameter to form the point; B the width of the hollow point at the base nearest the handle; C the length from the point to the base, and D the overall length from the point to the insertion of the loop ends into the handle end.

While the invention has been explained by a detailed description of certain specific embodiments, it is understood that various modifications and substitutions can be made in any of them within the scope of the appended claims which are intended also to include equivalents of such embodiments.

What is claimed is:

1. A personal toothpick comprising:
   a handle having an "S" shaped configuration for easy handling and manipulation,
   a first thin wire formed in a narrow and elongated "V" like configuration comprising a hollow point and having the ends of the wire form mounted to one end of the handle, the configuration of the wire form being dimensionally proportional for working on and into the crevices between teeth,
   a second active wire form mounted to the other end of the handle and comprising a narrow and elongated "V" having two legs diverging rearwardly for a predetermined distance towards the handle, each leg including an intermediate section projecting inwardly towards the opposite leg and an end portion extending in parallel to the handle,
   said handle including a recess at one end wherein the parallel end portions are mounted, said legs on the active wire form being capable of flexing inwardly to assume a smaller profile to accommodate the space between teeth.

2. A personal toothpick in accordance with claim 1 wherein at least one of the wire forms comprises:
   a semi-active wire end formed in a narrow and elongated "V" configuration having two legs, wherein one leg extends directly into a portion of the handle end and the other leg turns inwardly a predetermined distance from the handle end and includes a rear portion extending axially into the handle end, said handle end portion being recessed, the added length to the one leg increasing the flexibility of the wire form.

* * * * *